US008288085B2

(12) United States Patent  
Matsumoto et al.

(10) Patent No.: US 8,288,085 B2  
(45) Date of Patent: Oct. 16, 2012

(54) METHOD OF SEPARATING PANCREATIC ISLET

(75) Inventors: Shinichi Matsumoto, Kyoto (JP); Hiromi Wada, Kyoto (JP); Hirofumi Noguchi, Kyoto (JP)

(73) Assignee: Kyoto University, Kyoto-shi, Kyoto (JP)

( * ) Notice: Subject to any disclaimer, the term of this patent is extended or adjusted under 35 U.S.C. 154(b) by 710 days.

(21) Appl. No.: 11/793,679

(22) PCT Filed: Dec. 22, 2005

(86) PCT No.: PCT/JP2005/023602  
§ 371 (c)(1),  
(2), (4) Date: Oct. 22, 2007

(87) PCT Pub. No.: WO2006/068226  
PCT Pub. Date: Jun. 29, 2006

(65) Prior Publication Data  
US 2008/0038823 A1 Feb. 14, 2008

(30) Foreign Application Priority Data

Dec. 22, 2004 (JP) ................................ 2004-370732  
Jul. 21, 2005 (JP) ................................ 2005-211228

(51) Int. Cl.  
*A01N 1/00* (2006.01)  
*A01N 1/02* (2006.01)  
*A01N 63/02* (2006.01)

(52) U.S. Cl. ........................... 435/1.2; 435/1.1; 424/93.7

(58) Field of Classification Search ........................ None  
See application file for complete search history.

(56) References Cited

FOREIGN PATENT DOCUMENTS

| JP | 6-40801 | 2/1994 |
|---|---|---|
| JP | 2002-20309 | 1/2002 |

OTHER PUBLICATIONS

Ricordi et al in "Improved Human Islet Isolation Outcome From Marginal Donors Following Addition of Oxygenated Perfluorocarbon to the Cold-Storage Solution" (Transplantation, May 2003, vol. 75, No. 9, pp. 1524-1527).*
Kenmochi et al in "Improved Quality and Yield of Islets Isolated from Human Pancreata Using a Two-Step Digestion Method" (Pancreas, 2000, vol. 20, No. 2, pp. 184-190).*
2008 Mesh Headings for Gabexate.*
Rose et al in "An Evaluation of the Activation of Endogenous Pancreatic Enzymes During Human Islet Isolations", (Transplantation Proceedings, 2003, vol. 35, pp. 2455-2457).*
2008 Mesh Headings for Ulinistatin.*
2008 Mesh Headings for Nafamostat.*
Rose et al., "An evaluation of the activation of endogenous pancreatic enzymes during human islet isolations," *Transplantation Proceedings*, vol. 35, No. 7, Nov. 2003, pp. 2455-2457.
van der Burg et al., "Iodixanol density gradient preparation in university of Wisconsin solution for porcine islet purification," *The Scientific World Journal*, vol. 3, Dec. 1, 2003, pp. 1154-1159.
Chen et al., "Effective application of ET-Kyoto solution for clinical lung transplantation," *Transplantation Proceedings 2004*, vol. 36, No. 9, Nov. 2004, pp. 2812-2815.
Matsumoto et al., "The effect of two-layer (University of Wisconsin Solution/Perfluorochemical) preservation method on clinical grade pancreata prior to islet isolation and transplantation," *Transplantation Proceedings*, vol. 36, No. 4, May 2004, pp. 1037-1039.
Heiser et al., "Isolation of porcine pancreatic islets: Low trypsin activity during the isolation procedure guarantees reproducible high islet yields," *Journal of Clinical Laboratory Analysis*, vol. 8, No. 6, 1994, pp. 407-411.
Chadwick et al., "Storage of pancreatic digest before islet purification: Influence of colloids and the sodium to potassium ratio in University of Wisconsin-based preservation solutions," *Transplantation*, vol. 58, No. 1, Jul. 1994, pp. 99-1 04.
Beattie et al., "Trehalose: A cryoprotectant that enhances recovery and preserves function of human pancreatic islets after long-term storage," *Diabetes*, vol. 46, No. 3, Mar. 1, 1997, pp. 519-523.
Chen et al., "Development of new organ preservation solutions in Kyoto University," *Yonsei Medical Journal*, vol. 45, No. 6, 2004, pp. 1107-1114.
Noguchi et al., "Comparison of M-Kyoto solution and histidine-tryptophan-ketoglutarate solution with a trypsin inhibitor for pancreas preservation in islet transplantation," *Transplantation 2007*, vol. 84, pp. 655-658.
Noguchi et al., "Modified two-layer preservation method (M-Kyoto/PFC) improves islet yields in islet isolation," *American Journal of Transplantation 2006*, vol. 6, p. 496-504.
Shimizu, "Nafamostat mesilate rinse solution—A new strategy to prevent warm ischemia-reperfusion injury in canine pancreas autotransplantation," J. Kyoto Pref. Univ. Med., 1998, vol. 107, No. 4, pp. 483-497, especially p. 484, line 17 to 21.
Miyamoto et al., "Improved large-scale isolation of breeder porcine islets: Possibility of harvesting from non-heartbeating donor," Cell Transplantation, 1998. vol. 7, No. 4, pp. 397-402.
Kodu et al., "Rinsho Suito Ishoku no Tameno Suito Bunri Gijutsu (5)," Saisei Iryo, May 2004, vol. 3, No. 2, pp. 81-89.
Fujinaga et al., "Trehalose to Kekkan Naihi Hogo, Busshitsu o Fukumu Siabo Gaiekigata Zoki Hozoneki new ET-Kyoto Eki no Kaihatsu to Rinsho Oyo," The Journal of Japanse Society for Cryobiology and Cryotechnology, 2003, vol. 49, No. 2, pp. 107 to 108.
Plonne et al., "Separation of the intracellular secretory compartment of rat liver and isolated rat hepatocytes in a single step using self-generating gradients of iodizanol," Anal Biochem., 1999, vol. 276, No. 1, pp. 88-96.

(Continued)

*Primary Examiner* — Nancy T Vogel  
*Assistant Examiner* — Catherine Hibbert  
(74) *Attorney, Agent, or Firm* — Fitch, Even, Tabin & Flannery, LLP (57) ABSTRACT

The present invention provides a pancreatic islet isolation method comprising the steps of (1) injecting a protection solution containing a protease inhibitor into the pancreatic duct of an procured pancreas; (3) digesting the pancreas into which the protection solution has been injected; and (4) purifying the digested pancreatic tissue using a purification solution containing a density gradient reagent. The present invention also provides a protection solution for injection into the pancreatic duct, a pancreas preservation solution for the two-layer method, and an islet purification solution.

8 Claims, 4 Drawing Sheets

OTHER PUBLICATIONS

Matsumoto, Shinichi, et al."Improved Islet Yields from Macaca Nemestrina and Marginal Human Pancreata After Two-Layer Method Preservation and Endogenous Trypsin Inhibition", American Journal of Transplantation 2003: 3:53-63.

Basir, I., et al., "Improved Outcome of Pig Islet Isolation by Pefabloc Inhibition of trypsin", Transplanation Proceedings, 29, 1939-1941 (1997).

Sawada, Toshiya, et al., "Improved Islet Yield and Function with Ductal Injection of Univeersity of Wisconsin Solution Before Pancreas Preservation", Transplantation, vol. 75, 1965-1969, No. 12, Jun. 27, 2003.

Examination Report dated Nov. 19, 2010, corresponding with Australian Patent Application No. 2005320102.

Viaspan/University of Wisconsin Solution; (from Wikipedia, the free encyclopedia) retrieved from the Internet on Nov. 18, 2010 (2 pages). http://en.wikipedia.org/wiki/Viaspan.

S. Matsumoto et al., "Improved Islet Yields From Macaca Nemestrina and Marginal Human Pancreata After Two-Layer Method Preservation and Endogenous Trypsin Inhibition", American Journal of Transplantation, Jan. 2003, vol. 3, No. 1, pp. 53-63, ISSN 1600-6135.

* cited by examiner

A BLOOD GLUCOSE (mg/dl)

B INSULIN DOSE (U)

METHOD OF SEPARATING PANCREATIC ISLET

This application is the U.S. National Phase application under 35 U.S.C. §371 of PCT/JP2005/023602, filed Dec. 22, 2005, which was not published in English, claims the foreign priority benefit under 35 U.S.C. §119 of Japanese Application No. JP 2004-370732 filed Dec. 22, 2004 and Japanese Application No. JP 2005-211228 filed Jul. 21, 2005, and incorporates by reference the complete disclosures of the foresaid PCT and Japanese applications.

TECHNICAL FIELD

The present invention relates to a method of isolating pancreatic islets, which is a critical technology for pancreatic islet transplantation. More particularly, the present invention relates to a protection solution for injection into the pancreatic duct, a pancreas preservation solution for the two-layer method, and an islet purification solution, each of which is well-adapted for use in pancreatic islet isolation.

BACKGROUND ART

The technique of pancreatic islet transplantation into type-1 diabetic patients, who are unable to survive without the administration of insulin, that is, who are in an insulin dependent diabetes mellitus, is garnering a great deal of public awareness and efforts are being made, mainly in Europe and the United States, to establish this technique as a clinical treatment.

Pancreatic islet transplantation refers to cellular tissue transplantation in which pancreatic islet cell groups, which play a central role in blood sugar regulation in the body, are administered by infusion into the portal vein. Islet transplantation is minimally invasive for the transplant recipient and is regarded as the treatment nearest to ideal for type-1 diabetic patients.

In 2000, at the University of Alberta in Edmonton, Canada, a successful trial of clinical islet transplantation was reported. Since this report, approximately 300 islet transplantations have been performed in the 4 years, mainly in Europe and the United States. These islet transplantations have been carried out on the basis of the Edmonton protocol established at the University of Alberta.

However, with the technology heretofore, consistent islet yields have not been obtained, even in islet transplantation from brain-dead donors carried out in Europe and the United States, and in some instances the transplanted islets have also not functioned effectively. Moreover, even when considered on a worldwide basis, there have been almost no successful cases of islet transplantation from non-heart-beating donors, where the conditions are worse than with brain-dead donors, and in fact islet transplantation from non-heart-beating donors has to date not been possible.

To raise the success rates of islet transplantation and also to achieve successful islet transplantation from non-heart-beating donors, it is important to transplant a large population of islets fit for transplantation. Therefore, there has been strong demand for improvements in islet isolation technology in order to raise the yield of transplantable islets.

On the other hand, in the medical treatment of transplantation, a method has been reported in which ulinastatin or a ulinastatin substitute is administered post-transplant to organ transplant patients (See Japanese Unexamined Patent Publication No. 2002-20309).

Further, a solution for perfusion or storage of organs that are destined for transplantation has been reported, wherewith excellent results were obtained in lung transplantation (refer to Japanese Unexamined Patent Publication No. H6-40801).

However, an optimal means for islet transplantation, particularly with regard to islet isolation and purification technology, remains elusive.

DISCLOSURE OF THE INVENTION

Problems to be Solved by the Invention

A main object of the present invention is to provide islet isolation techniques that can improve the yield of transplantable islets.

Means for Solving the Problems

The present inventors conducted varied and extensive investigations with the main goal of improving islet yields, and as a result, they found that the yield of transplantable islets is raised by the use of special solutions and methods. They conducted further intensive research and achieved the present invention.

That is, the present invention relates to the following isolation methods and solutions.

Item 1: A pancreatic islet isolation method comprising the steps of:
(1) injecting a protection solution containing a protease inhibitor into the pancreatic duct of an procured pancreas;
(3) injecting an enzyme solution into said pancreas into which the protective solution has been injected and digesting the pancreas; and
(4) purifying the digested pancreas tissue using a purification solution containing a density gradient reagent.

Item 2: An isolation method according to Item 1, wherein the protection solution is injected into the pancreatic duct at the rate of approximately 0.1 to 10 ml per 1 gram organ weight in step (1).

Item 3: An isolation method according to Item 1 or 2, wherein the protease-inhibitor-containing protection solution has a potassium concentration of approximately 4 to 50 mmol/L.

Item 3A: An isolation method according to any of Items 1 to 3, wherein the protease-inhibitor-containing protection solution further contains trehalose.

Item 4: An isolation method according to any of Items 1 to 3A, further comprising (2) a step of preserving the protection-solution-injected pancreas by a two-layer method.

In other words, a pancreatic islet isolation method, comprising the steps of:
(1) injecting a protection solution containing a protease inhibitor into the pancreatic duct of an procured pancreas;
(2) preserving by the two-layer method the pancreas into which the protection solution has been injected;
(3) introducing an enzyme solution into the pancreas after preservation and digesting the pancreas; and
(4) purifying the digested pancreas tissue using a purification solution containing a density gradient reagent.

Item 5: An isolation method according to Item 4, wherein the two-layer method of step (2) is a two-layer method that uses (i) a liquid perfluorocarbon and (ii) a preservation solution that contains a protease inhibitor and has a potassium concentration of approximately 4 to 50 mmol/L.

Item 5A: An isolation method according to Item 5, wherein the preservation solution (ii) further contains trehalose.

Item 6: An isolation method according to any of Items 1 to 5A, wherein the purification solution in step (4) further contains trehalose.

Item 7: An isolation method according to any of items 1 to 6, wherein the density gradient reagent in step (4) is iodixanol.

Item 8: An isolation method according to any of Items 1 to 7, wherein the purification solution in step (4) further contains a protease inhibitor.

Item 8A: An isolation method according to any of Items 1 to 8, wherein the protease inhibitor is at least one selected from the group consisting of ulinastatin, gabexate mesilate, and nafamostat mesilate.

Item 9: A protection solution for injection into the pancreatic duct that contains a protease inhibitor.

In an alternative formulation, a use of a protease-inhibitor-containing protection solution is for injection into the pancreatic duct during islet isolation. The protease inhibitor is preferably at least one selected from the group consisting of ulinastatin, gabexate mesilate, and nafamostat mesilate.

Item 10: A protection solution according to Item 9 that has a potassium concentration of approximately 4 to 50 mmol/L.

Item 10A: A protection solution according to Item 9 or 10 that further contains trehalose.

Item 11: A pancreas preservation solution for a two-layer method that contains a protease inhibitor and has a potassium concentration of approximately 4 to 50 mmol/L.

In other words, a use of a preservation solution containing a protease inhibitor and having a potassium concentration of approximately 4 to 50 mmol/L for pancreas preservation by the two-layer method during islet isolation.

The protease inhibitor is preferably at least one selected from the group consisting of ulinastatin, gabexate mesilate, and nafamostat mesilate.

Item 11A: A preservation solution according to Item 11 that further contains trehalose.

Item 12: A pancreatic islet purification solution that contains a density gradient reagent and trehalose.

In other words, a use of a solution containing trehalose and a density gradient reagent for islet purification during islet isolation.

Item 13: A purification solution according to Item 12, wherein the density gradient reagent is iodixanol.

In other words, a purification solution that contains iodixanol and trehalose.

Item 14: The purification solution according to Item 12 or 13 that further contains a protease inhibitor.

In other words, the purification solution according to Item 12 or 13, that contains a density gradient reagent, trehalose, and a protease inhibitor.

The protease inhibitor is preferably at least one selected from the group of ulinastatin, gabexate mesilate, and nafamostat mesilate.

The present invention also encompasses the following modes.

Item 15: A method of pancreatic islet isolation comprising the steps of:

(1) injecting a tissue protection or preservation solution that contains a trypsin inhibitor into the pancreatic duct of an procured pancreas;

(2) distending the pancreas by injecting a collagenase solution into the aforesaid pancreas into which the protection or preservation solution has been injected;

(3) activating the collagenase by raising the temperature of the solution within the distended pancreas and thereby digesting the pancreatic tissue;

(4) recovering the digested pancreatic tissue; and (5) purifying the islets by isolating the islets from the recovered pancreatic tissue.

Item 16: An isolation method according to Item 15, wherein step (5) comprises the following steps (5-1) to (5-3) of:

(5-1) setting up a density gradient in a purification solution comprising a tissue protection or preservation solution to which a density gradient reagent has been added;

(5-2) adding the recovered pancreatic tissue to the purification solution in which a density gradient has been set up; and (5-3) purifying the islets by isolating the islets from the pancreatic tissue by centrifugally separating the purification solution to which the pancreatic tissue has been added.

Item 17: An isolation method according to Item 16, wherein step (5-1) is a step (5-1') comprising:

(5-1') setting up a density gradient in a purification solution comprising a tissue protection or preservation solution to which a trypsin inhibitor and a density gradient reagent have been added.

Item 18: An isolation method according to Item 16 or 17, wherein the density gradient reagent is iodixanol.

Item 19: An isolation method according to any of items 15 to 18 that further contains the following step comprising:

(1-2) preserving the pancreas into which the protection or preservation solution has been injected, in a container in which there are formed two layers: a layer comprising perfluorocarbon and a layer comprising a tissue protection or preservation solution that contains a trypsin inhibitor.

Item 20: An isolation method according to any of Items 15 to 19, wherein the trypsin inhibitor is ulinastatin.

Item 21: An isolation method according to any of Items 15 to 20, wherein the potassium concentration of the tissue protection or preservation solution is 4 to 50 mmol/L.

Item 22: A pancreatic islet purification solution comprising a tissue protection or preservation solution that has a potassium concentration of 4 to 50 mmol/L and to which iodixanol has been added.

Item 23: A purification solution according to item 22, to which a trypsin inhibitor has further been added.

Item 24: A purification solution according to item 23, wherein the trypsin inhibitor is ulinastatin.

The present invention is described in more detail in the following.

I. Pancreatic Islet Isolation Method

The pancreatic islet isolation method of the present invention comprises the steps of:

(1) injecting a protection solution containing a protease inhibitor into the pancreatic duct of an procured pancreas;

(3) injecting an enzyme solution into the protection solution-injected-pancreas and digesting the pancreas; and (4) purifying the digested pancreatic tissue using a purification solution containing a density gradient reagent.

The present invention also encompasses the method that further contains the step of:

(2) preserving the protection-solution-injected-pancreas using the two-layer method.

I(1). Step of Injecting a Protection Solution into the Pancreatic Duct

The isolation method of the present invention includes a step of injecting a protease-inhibitor-containing protection solution into the pancreatic duct of a pancreas that has been procured from the donor. By injecting the protease-inhibitor-containing preservation solution into the pancreatic duct, the pancreatic tissue is appropriately protected and the yield of transplantable islets is increased.

The volume of protection solution injected into the pancreatic duct can be established as appropriate according to the state of the organ or the like and is approximately 0.1 to 10 ml, preferably approximately 0.1 to 2 ml, and more preferably approximately 1 to 1.5 ml, in each case per 1 gram organ weight.

The injection of such amounts is preferred from the standpoint of enabling an appropriate perfusion of the protection solution into the pancreatic duct of the entire pancreas and thereby raising the yield of good quality islets.

The protease inhibitor can be selected as appropriate, but at least one selected from the group consisting of ulinastatin, gabexate mesilate, and nafamostat mesilate is particularly preferred from the standpoint of obtaining an even better islet yield.

The protection solution preferably has a low potassium concentration from the standpoint of improving the yield of transplantable islets. In specific terms, a potassium concentration of 4 to 50 mM, particularly 10 to 50 mM, per 1000 mL protection solution is preferred.

The protection solution preferably further contains trehalose from the standpoint of increasing the yield of transplantable islets.

The timing of protection solution injection can be established as appropriate, but is preferably as soon as possible and is preferably immediately after procurement of the pancreas.

The method of injecting the protection solution can be established as appropriate; for example, a catheter can be inserted into the procured pancreas and injection can be carried out through this catheter using a pump while regulating the injection pressure.

The number of inserted catheters can be selected as appropriate, but preferably a single catheter is employed. The use of a single catheter minimizes leakage of the solution injected into the organ and enables a more precise injection of the solution and can also reduce damage to the organ.

I(2). Step of Preservation Using the Two-Layer Method

After the protection solution has been injected into the pancreatic duct, the pancreas is preferably preserved using the two-layer method.

This two-layer method can be implemented by introducing a liquid perfluorocarbon and a preservation solution into a container so as to form two layers; then feeding oxygen into the container; and preserving the pancreas in an immersed state in the container. The proportion between the liquid perfluorocarbon and preservation solution is about 1:1 as a volume ratio. The oxygen feed is preferably carried out for at least 30 minutes.

Preservation of the pancreas by the two-layer method enables a high level of tissue viability to be maintained.

The preservation solution used in the two-layer method preferably contains a protease inhibitor. The islet yield can be increased through this use of a protease-inhibitor-containing preservation solution.

The protease inhibitor can be selected as appropriate, but at least one selected from the group consisting of ulinastatin, gabexate mesilate, and nafamostat mesilate is particularly apt from the standpoint of obtaining an even better islet yield.

The preservation solution preferably has a low potassium concentration. In specific terms, the potassium concentration is preferably about 4 to 50 mmol/L and particularly preferably about 10 to 50 mmol/L.

The use of a preservation solution with a low potassium concentration enables a further increase in the islet yield to be obtained.

Additionally, the preservation solution preferably further contains trehalose. The use of a preservation solution that contains trehalose enables a further increase in the islet yield to be obtained.

I(3). Step of Digesting the Pancreas

Digestion of pancreatic tissue is then carried out on the pancreas into which protection solution has been injected or on the pancreas that has been preserved by the two-layer method.

Digestion, i.e. degradation, can be carried out, for example, by distending the pancreas by injecting an enzyme solution into the duct of the pancreas and then raising the temperature of the enzyme solution in order to effect enzyme activation.

Enzyme solution injection can be carried out, for example, by injecting the enzyme solution into the main pancreatic duct using a pump while controlling the injection pressure. The enzyme solution can be injected through the same catheter as used for injection of the protection solution.

As the enzyme solution, a collagenase solution can be used, for example.

After the enzyme solution has been injected into the pancreas, digestion can be started by raising the temperature of the solution using a suitable device.

For example, when a collagenase solution is employed, the distended pancreas is placed in a Ricordi chamber; the digestion circuit is filled with the solution; and the system is closed. The solution is circulated by a pump and the temperature of the solution is raised to around body temperature at about 37° C. The collagenase injected into the pancreatic tissue is activated when the temperature is raised, resulting in digestion of the pancreatic tissue through the dissolution of collagen, which forms a tissue that binds the cells to each other.

Digestion is halted at the point at which just the pancreatic exocrine tissue has been dissociated from around the islets while the cells making up the islets remain intact in their aggregated state.

Digestion can be halted by lowering the temperature of the solution. Digestion can also be halted by deactivating the enzyme by adding serum protein.

For example, digestion can be halted by converting the circulation path to an open system and passing a room-temperature solution containing human albumin through the circulation path. The passage of a room-temperature solution can lower the solution temperature and can also dilute the enzyme. The activity of the enzyme can also be reduced by the addition of serum protein.

The pancreatic tissue is recovered after digestion has been stopped. The recovered pancreatic tissue is preferably centrifugally washed and concentrated with a centrifugal separator prior to purification.

I(4). Purification Step

Purification can be carried out utilizing the fact that the islets have a lighter specific gravity than pancreatic exocrine tissue. For example, the digested pancreatic tissue can be added to a solution in which a density gradient, i.e., a specific gravity concentration gradient, has been formed and the islets can be purified by separation of the islets from the pancreatic exocrine tissue by density gradient and centrifugation.

The following procedure, for example, can be used.

First, a density gradient is formed in a purification solution that contains a density gradient reagent.

Then, the digested pancreatic tissue is added to the purification solution in which the density gradient is formed.

The purification solution loaded with the digested pancreatic tissue is then subjected to centrifugal separation by density gradient and centrifugation. Separating the islets from the exocrine tissue by this centrifugal separation, and the islets are isolated from the recovered pancreatic tissue.

A density gradient reagent that can form a low viscosity solution is preferred. Suitable density gradient reagents include Iodixanol (Optiprep™ brand reagent) and N,N'-bis (2,3-dihydroxypropyl)-5-[N-(2,3-dihydroxypropyl)acetoamido]-2,4,6-triiodo-isophthalamide (NYCODENZ® brand reagent).

The purification solution preferably additionally contains a protease inhibitor. A purification solution containing a protease inhibitor can further improve the islet yield.

The density gradient may be either a continuous density gradient or a discontinuous density gradient; however, a continuous density gradient is preferred because it enables the recovery of more islets.

The density gradient can be formed as appropriate by known methods. Appropriate apparatus can be used, for example, an instrument that forms a continuous density gradient.

A cell processor, such as a COBE® 2991 brand cell processor, can also be utilized for purification.

For example, a density gradient can be formed in the COBE® 2991 brand cell processor using a density gradient reagent; the digested pancreatic tissue, after washing and concentration, can be added thereto; and, after the islets have been separated from the exocrine tissue by continuous density gradient and centrifugation, the solution in the cell processor (COBE® 2991 brand processor) can be recovered in individual fractions. After separation, the microscopic inspection of the solution is carried out to determine which fractions contain the islets and recover the islets.

This recovery of the purified islets completes the series of isolation steps.

II. Protection Solution for Injection into Pancreatic Duct

The protection solution of the present invention can be used for injection into the pancreatic duct during the isolation of islets for islet transplantation. In addition, the protection solution of the present invention can be very suitably used as the protease-inhibitor-containing protection solution in the isolation method of the present invention described above.

The protection solution of the present invention can be obtained by adding a protease inhibitor to a tissue protection or preservation solution.

II-1. Protease Inhibitor

The protease inhibitor used in the present invention is not particularly limited by its origin and type, as long as it has protease-inhibiting activity. Known protease inhibitors can be suitably used, but a trypsin inhibitor having a trypsin-inhibiting activity is particularly preferred.

Examples of protease inhibitors include at least one selected from the group consisting of ulinastatin (Miraclid™ brand injectable formulation of ulinstatin), 4-[2-aminoethyl-benzenesulfonyl]fluoride (AEBSF, Pefabloc™ brand protease inhibitor), gabexate mesilate (FOY™ brand protease inhibitor), and nafamostat mesilate (Fusan™ brand protease inhibitor). Among these, at least one selected from the group consisting of ulinastatin, gabexate mesilate, and nafamostat mesilate is preferred for use from the standpoint of further improving the islet yield. Ulinastatin and gabexate mesilate are also preferred for their anti-inflammatory activity.

The rate of addition of the protease inhibitor to the protection solution can be established as appropriate in accordance with the type of inhibitor and within a range in which the effects of the present invention are achieved. When the protease inhibitor is ulinastatin, the rate of addition is about 10,000 to 100,000 Upper liter and preferably about 50,000 to 100,000 Upper liter. When the protease inhibitor is gabexate mesilate, the rate of addition is about 100 to 10,000 mg per liter and preferably about 500 to 2,000 mg per liter.

II-2. Tissue Protection or Preservation Solution

The tissue protection or preservation solution can be selected suitably from known solutions used for the protection or preservation of tissue (including organs and cells).

For example, Euro-Collins solution, University of Wisconsin solution (UW solution), ET-Kyoto solution, Low-Potassium Dextran Glucose solution, HTK solution (Custodiol™ brand solution), and so forth can be used.

Solutions with the compositions given below can also be provided as examples.

Tissue Protection or Preservation Solution (Example 1)

| | |
|---|---|
| Sodium ($Na^+$) | 10 to 140 mmol/L |
| Potassium ($K^+$) | 4 to 140 mmol/L |
| Magnesium ($Mg^{2+}$) | 0 to 4 mmol/L |
| Calcium ($Ca^{2+}$) | 0 to 2 mmol/L |
| Phosphate ($H_2PO_4^-$ or $HPO_4^{2-}$) | 12 to 65 mmol/L |
| $Cl^-$, $HCO_3^-$, $CO_3^{2-}$, organic acid, or organic acid anion | 15 to 150 mmol/L |
| Hydroxyl ethyl starch | 0 to 80 g/L |
| Trehalose | 0 to 240 mmol/L |

Tissue Protection or Preservation Solution (Example 2)

| | |
|---|---|
| Sodium ($Na^+$) | 10 to 140 mmol/L |
| Potassium ($K^+$) | 4 to 140 mmol/L |
| Hydroxyethyl starch | 0 to 80 g/L |
| Glutathione | 0 to 10 mmol/L |
| Adenosine | 0 to 10 mmol/L |
| Lactobionate | 0 to 140 mmol/L |
| Raffinose | 0 to 50 g/L |

Tissue Protection or Preservation Solution (Example 3)

| | |
|---|---|
| Sodium ($Na^+$) | 80 to 120 mmol/L |
| Potassium ($K^+$) | 4 to 50 mmol/L |
| Gluconate | 15 to 150 mmol |
| Phosphate | 20 to 40 mmol/L |
| Trehalose | 80 to 160 mmol/L(27 to 55 g/L) |
| Hydroxyl ethyl starch (HES) | 20 to 60 g/L |
| Dibutyryl cAMP | 0 to 10 mmol/L |
| Nitroglycerin | 0 to 1 g/L |

Among the tissue protection or preservation solutions provided as examples above, the ET-Kyoto solution, the solution described in example 1, and the solution described in example 3 are particularly preferred.

II-3. Embodiments of the Protection Solution for Injection into Pancreatic Duct

The protection solution for injection into the pancreatic duct preferably has a low potassium concentration. In specific terms, a potassium concentration of 4 to 50 mM, particularly 10 to 50 mM per 1000 mL protection solution is preferred.

The use of a low potassium concentration avoids the induction of vasospasm and can thereby prevent insulin release from the islets and enable the solution to quickly spread throughout the tissue. This results in an even higher pancreatic duct protection action and improves the yield of transplantable islets.

The osmolarity of the protection solution for injection into the pancreatic duct is preferably 270 to 450 mOsm/L and particularly preferably is 300 to 400 mOsm/L. Swelling or shrinkage of the tissue during protection or preservation can be prevented within this range.

The pH of the protection solution for injection into the pancreatic duct is preferably about 7 to 8 in order to stop acidic degradation of the cells and tissue.

The protection solution for injection into the pancreatic duct preferably contains trehalose. The presence of trehalose provides an additional increase in protective action on the pancreatic duct and can thereby improve the islet yield. Trehalose exists in three forms, i.e. α,α-trehalose, α,β-trehalose, and β,β-trehalose; any of these may be used and their mixtures may be used. α,α-Trehalose, present in nature, is preferably used.

Trehalose concentration is about 0 to 400 mmol, particularly about 50 to 240 mmol, and even more particularly about 80 to 160 mmol, in each case per 1000 mL of the protection solution.

The protection solution for injection into the pancreatic duct may also contain other components insofar as the effects of the present invention are not impaired. These other components can be exemplified by various electrolytes, sugars, amino acids, drugs, vitamins, and so forth.

The protection solution for injection into the pancreatic duct may also contain a cell activator such as AMP (e.g., dibutyryl cAMP) or ATP, a vasodilator such as prostaglandin or nitroglycerin, antibiotics, adenosine, N-acetyl-L-cysteine, glycine, ascorbic acid, glutamine, nicotinamide, glutathione, raffinose, and so forth.

A solution containing at least the following components in the following proportions is an example of a preferred embodiment of the protection solution according to the present invention for injection into the pancreatic duct.

| | |
|---|---|
| Sodium | 80 to 120 mmol/L |
| Potassium | 4 to 50 mmol/L |
| Gluconate | 15 to 150 mmol/L |
| Phosphate | 20 to 40 mmol/L |
| Trehalose | 80 to 160 mmol/L |
| Hydroxyl ethyl starch (HES) | 20 to 60 g/L |
| Ulinastatin | 10,000 to 100,000 U/L |

The protection solution according to the present invention for injection into the pancreatic duct has a high protective action on the pancreatic duct and can keep the tissue viablity and can stabilize and satisfactorily protect the tissue and as a result can raise the yield of transplantable islets.

III. Pancreas Preservation Solution for the Two-Layer Method

The preservation solution according to the present invention can be used for pancreas preservation by the two-layer method during the isolation of islets for islet transplantation. In addition, the pancreas preservation solution according to the present invention for the two-layer method can be very suitably used as the preservation solution used in the two-layer method in the islet isolation method of the present invention described above.

The preservation solution according to the present invention can be obtained by the addition of a protease inhibitor to a tissue protection or preservation solution that has a low potassium concentration.

The inhibitors described in II-1 above can be used as the instant protease inhibitor.

The low-potassium versions of the solutions described in II-2 above can be used as the tissue protection or preservation solution. ET-Kyoto solution is particularly preferred.

III-2. Embodiments of Pancreas Preservation Solution for the Two-Layer Method

The amount of protease inhibitor to be added to the preservation solution can be established as appropriate in accordance with the type of inhibitor and within a range in which the effects of the present invention are achieved.

When the protease inhibitor is ulinastatin, the amount to be added is about 10,000 to 100,000 Upper liter and preferably about 50,000 to 100,000 Upper liter. When the protease inhibitor is gabexate mesilate, the amount to be added is about 100 to 10,000 mg per liter and preferably about 500 to 2000 mg per liter.

The potassium concentration in the pancreas preservation solution for the two-layer method is about 4 to 50 mM and particularly 10 to 50 mM.

The use of a low potassium concentration provides an even more satisfactory pancreas preservation activity and can thereby improve the yield of transplantable islets.

The osmolarity of the preservation solution is preferably 270 to 450 mOsm/L and is particularly preferably 300 to 400 mOsm/L. Swelling or shrinkage of the tissue during preservation can be prevented within this range.

The pH of the preservation solution is preferably about 7 to 8 in order to prevent acidic degradation of the cells and tissue.

The preservation solution preferably contains trehalose.

Trehalose concentration is about 0 to 400 mmol, particularly about 50 to 240 mmol, and even more particularly about 80 to 160 mmol, in each case per 1000 mL the preservation solution. The presence of trehalose provides an additional increase in pancreas protection activity and can thereby increase the islet yield.

The preservation solution may also contain other components insofar as the effects of the present invention are not impaired. These other components can be exemplified by various electrolytes, sugars, amino acids, drugs, vitamins, and so forth.

The preservation solution may also contain a cell activator such as AMP (e.g., dibutyryl cAMP) or ATP, a vasodilator such as prostaglandin or nitroglycerin, antibiotics, adenosine, N-acetyl-L-cysteine, glycine, ascorbic acid, glutamine, nicotinamide, glutathione, raffinose, and so forth.

A solution containing at least the following components in the following proportions is an example of a preferred embodiment of the preservation solution according to the present invention for use in the two-layer method.

| | |
|---|---|
| Sodium | 80 to 120 mmol/L |
| Potassium | 4 to 50 mmol/L |
| Gluconate | 15 to 150 mmol/L |
| Phosphate | 20 to 40 mmol/L |
| Trehalose | 80 to 160 mmol/L |
| Hydroxyl ethyl starch (HES) | 20 to 60 g/L |
| Ulinastatin | 10,000 to 100,000 U/L |

Use of the preservation solution according to the present invention provides a highly protective action on the pancreas and can keep the tissue viability intact and can satisfactorily preserve the tissues thereof, and as a result can substantially improve the yield of transplantable islets.

IV. Islet Purification Solution

The purification solution of the present invention is well-adapted for islet purification in islet isolation during islet transplantation. In addition, the purification solution according to the present invention is well-adapted for use as the purification solution in the islet isolation method according to the present invention described above.

The purification solution according to the present invention can be obtained by adding a density gradient reagent to a tissue protection or preservation solution that contains trehalose. The trehalose-containing versions of the solutions described in II-2 above can be used as this trehalose-containing tissue protection or preservation solution. The use of ET-Kyoto solution is particularly preferred.

IV-1. Density Gradient Reagent

The density gradient reagent can be selected as appropriate from known density gradient reagents used to prepare a density gradient in a solution. A density gradient reagent that can form a low-viscosity solution is particularly preferred. It is also preferred that the density gradient reagent have a low endotoxin level.

Suitable examples of the density gradient reagent include iodixanol (Optiprep™ brand density gradient reagent) and N,N'-bis(2,3-dihydroxypropyl)-5-[N-(2,3-dihydroxypropyl) acetoamido]-2,4,6-triiodo-isophthalamide (NYCODENZ® brand density gradient reagent). Iodixanol is particularly suitable.

Using these as the density gradient reagent makes it possible to obtain a low-viscosity purification solution and can expedite the purification speed. In addition, they can provide solutions with a low endotoxin level.

The mixing proportion of the density gradient reagent with respect to the tissue protection or preservation solution can be established as appropriate by measuring the density of the pancreas tissue prior to purification and considering the specific gravity of the density gradient reagent and the tissue protection or preservation solution.

IV-2. Trehalose

Trehalose exists in three forms, i.e. α,α-trehalose, α,β-trehalose, and β,β-trehalose; any of these may be used and their mixtures may be used. α,α-Trehalose, present in nature, is preferably used.

The trehalose concentration in the purification solution is about 0 to 400 mmol/L, particularly 50 to 240 mmol/L, and even more particularly about 80 to 160 mmol/L.

IV-3. Protease Inhibitor

The purification solution preferably also contains a protease inhibitor. The protease inhibitors described in II-1 above can be used as this protease inhibitor. In particular, at least one selected from the group consisting of ulinastatin, gabexate mesilate, and nafamostat mesilate is preferred from the standpoint of further improving the islet yield.

In those cases where a protease inhibitor is added to the purification solution, the rate of addition can be established as appropriate in accordance with the type of inhibitor and within a range in which the effects of the present invention are achieved.

When the protease inhibitor is ulinastatin, the amount to be added is about 10,000 to 100,000 Upper liter and preferably about 50,000 to 100,000 Upper liter. When the protease inhibitor is gabexate mesilate, the amount to be added is about 100 to 10,000 mg per liter and preferably about 500 to 2,000 mg per liter.

IV-4. Embodiments of the Purification Solution

The purification solution preferably has a low potassium concentration, wherein about 4 to 50 mmol/L is preferred and about 10 to 50 mmol/L is particularly preferred.

The purification solution preferably has a low viscosity. In particular, the viscosity measured by the Brookfield method at a measurement temperature of 22° C. should be no greater than 5 centipoise (cP), preferably no greater than 3 cP, and more preferably no greater than 2 cP.

Other components may be added as appropriate to the purification solution insofar as the effects of the present invention are not impaired. These other components encompass, for example, adenosine, dextran, heparin, and so forth.

An example of a preferred embodiment of the purification solution is a solution containing at least the following components in the following proportions:

| | |
|---|---|
| Sodium | 80 to 120 mmol/L |
| Potassium | 4 to 50 mmol/L |
| Gluconate | 15 to 150 mmol/L |
| Phosphate | 20 to 40 mmol/L |
| Trehalose | 80 to 160 mmol/L |
| Hydroxyl ethyl starch (HES) | 20 to 60 g/L |
| Iodixanol | 100 to 500 mL/L |

An example of a preferred embodiment of the protease-inhibitor-containing purification solution is a solution containing at least the following components in the following proportions:

| | |
|---|---|
| Sodium | 80 to 120 mmol/L |
| Potassium | 4 to 50 mmol/L |
| Gluconate | 15 to 150 mmol/L |
| Phosphate | 20 to 40 mmol/L |
| Trehalose | 80 to 160 mmol/L |
| Hydroxyethyl starch (HES) | 20 to 60 g/L |
| Iodixanol | 100 to 500 mL/L |
| Ulinastatin | 10,000 to 100,000 U/L |

In islet purification for transplantation, it is crucial that islet purification be carried out in such a manner that the three-dimensional structure of the islets is preserved. The use of the purification solution according to the present invention makes it possible to raise the yield of transplantable islets residing in a state in which the three-dimensional structure of the islets has been well maintained.

V. Islet Transplantation

Islet transplantation can be carried out by infusing the islets obtained by the series of isolation steps described above into the portal vein of a patient.

When the isolated islets satisfy established criteria, they are judged as suitable for transplantation and are then used for transplantation.

Viewed from the perspective of efficacy, determination as to whether the islets to be used for transplantation will function as islets post-transplantation is required. In addition, the risk of introducing pathogens, toxic substance, and so forth into the recipient must be excluded to the maximum extent possible.

In specific terms, the following criteria are used for transplantation-qualified isolated islets.

Islet Yield ≧4,000 IE/kg (patient body weight)
Purity ≧30%
Tissue volume ≦10 ml
Viability ≧70%
Endotoxin ≧5 IE/kg (patient body weight)
Negative Gram stain An islet yield ≧5,000 IE/kg (Patient body weight) is more appropriate for carrying out islet transplantation more efficiently.

Islets that have been evaluated as qualified for transplantation are preserved until the patient (recipient) can be prepared. Once the patient has been prepared, administration is carried out into the portal vein by infusion.

As necessary, various known techniques for islet transplantation and islet isolation can be added to the technology according to the present invention for islet isolation.

The present invention increases the yield of transplantable islets. The present invention can also raise the efficiency of purification and can improve the speed of purification. This in turn makes it possible to transplant large numbers of good-quality islets and can bring about a more effective post-transplant islet functionality.

The use of the isolation method and solutions according to the present invention can improve clinical outcome resulting from islet transplantation.

Effect of the Invention

The islet isolation method of the present invention increases the yield of transplantable islets. It also enables islet isolation to be carried out at efficiently in a shorter period of time.

The islet isolation method of the present invention is characterized by the injection of a protease-inhibitor-containing protection solution into the pancreatic duct.

This injection of a protease-inhibitor-containing protection solution into the pancreatic duct provides good protection for the pancreatic tissue in the pancreatic duct and thereby improves the yield of transplantable islets.

The isolation method of the present invention may also incorporate a step of preserving the pancreas using the two-layer method. Preservation using the two-layer method is preferably carried out using (i) liquid perfluorocarbon and (ii) a preservation solution that contains a protease inhibitor and that has a potassium concentration of 4 to 50 mmol/L. This provides a remarkable improvement in the yield of transplantable islets.

The isolation method of the present invention further comprises a step of purification using a purification solution that contains a density gradient reagent. Purification is preferably carried out using a purification solution that contains a density gradient reagent and trehalose. Purification is more preferably carried out using a purification solution that further contains a protease inhibitor. The use of these purification solutions raises the efficiency of purification and also improves the cells of the islets fit for transplantation.

The isolation method of the present invention, because it has the characteristic features cited above, is also characterized by its ability to bring about a substantial increase in the yield of transplantable islets.

The present invention further provides a protease-inhibitor-containing protection solution for injection into the pancreatic duct. This protection solution has a highly protective effect upon the pancreatic duct and thereby brings about an increase in the islet yield.

The present invention further provides a pancreas preservation solution for the two-layer method, said solution containing protease inhibitor and having a potassium concentration of 4 to 50 mmol/L. This preservation solution is highly protective of the pancreas and maintains tissue viability and provides thorough tissue protection, thereby increasing the yield of transplantable islets.

The present invention further provides an islet purification solution that contains a density gradient reagent and trehalose. The present invention further provides a purification solution that contains a density gradient reagent, trehalose, and a protease inhibitor. These purification solutions can raise the efficiency of purification and can also raise the yield of transplantable islets. The lowered viscosity of these purification solutions can boost the speed of purification. Moreover, they have low endotoxin levels and can also lower the risk to the patient.

Thus, the present invention provides an islet isolation method, a protection solution for injection into the pancreatic duct, a pancreas preservation solution for the two-layer method, and an islet purification solution, each of which can raise the yield of transplantable islets.

The present invention raises the yield of islets that satisfy the qualifying criteria for transplantation and as a consequence can increase the success rate of islet transplantation. Moreover, the present invention makes it possible to realize islet transplantation from non-heart-beating donors, which in fact has not been possible with prior-art methods.

As a consequence of the preceding, the present invention can provide a more reliable and more effective treatment for insulin-dependent diabetics and particularly type-I diabetic patients and substantially contributes to the clinical implementation of islet transplantation.

BEST MODE FOR CARRYING OUT THE INVENTION

The present invention is described in the following, using examples and experimental examples in order to further elucidate the present invention; however, the present invention is not limited to these examples.

Materials and Methods
1. Materials
1(1): Protection Solutions and Preservation Solutions UW solution (ViaSpan™ brand solution, made by DuPont) and ET-Kyoto solution (Kyoto Solution, Kyoto Biomedical Science Co., Ltd.) were used.

ET-Kyoto+ulinastatin solution (hereinafter also referred to as M-Kyoto solution) was also prepared by adding 100,000 units (U) ulinastatin (Miraclid™ brand injectable solution of ulinastatin, Mochida Pharmaceutical Co., Ltd.) to 1 L ET-Kyoto solution.

The composition of the main components present in UW solution, ET-Kyoto solution, and M-Kyoto solution and the osmolarity are given in Table 1.

TABLE 1

|  | UW Solution | ET-Kyoto Solution | M-Kyoto Solution |
|---|---|---|---|
| Sodium (Na) (mmol/L) | 29 | 100 | 100 |
| Potassium (K) (mmol/L) | 125 | 43.5 | 43.5 |
| Magnesium (Mg) (mmol/L) | 5 | — | — |
| Gluconate (mmol/L) | — | 100 | 100 |
| Phosphate (mmol/L) | 25 | 25 | 25 |
| Sulfate (mmol/L) | 5 | — | — |
| Lactobionate (mmol/L) | 100 | — | — |
| Raffinose (mmol/L) | 30 | — | — |
| Trehalose (mmol/L) | — | 120 | 120 |
| Adenosine (mmol/L) | 5 | — | — |
| Allopurinol (mmol/L) | 1 | — | — |
| Glutathione (mmol/L) | 3 | — | — |
| Hydroxy Ethyl Starch (HES) (g/L) | 50 | 30 | 30 |
| Ulinastatin ($\times 10^3$ U/L) | — | — | 100 |
| Osmorality (mOsm) | 320 | 366 | 366 |

ET-Kyoto+Pefabloc solution was prepared by adding 0.4 to 8 mM 4-[2-aminoethylbenzenesulfonyl]fluoride·HCl (AEBSF, Pefabloc™ brand protease inhibitor, made by Roche Diagnostics) to 1 L ET-Kyoto solution.

ET-Kyoto+FOY solution was prepared by adding 1000 mg gabexate mesilate (FOY™ brand protease inhibitor, made by Ono Pharmaceutical Co., Ltd.) to 1 L ET-Kyoto solution.

1(2). Purification Solutions

Ficoll solution was prepared by mixing two Ficoll solutions (Ficoll™ brand solution, Pharmacia Corporation) having different concentrations (dilution with Hanks' solution) so as to provide a light specific gravity of about 1.07 to 1.08 and a heavy specific gravity of 1.09 to 1.12.

ET-Kyoto+iodixanol solution (hereinafter also referred to as I-Kyoto solution) was prepared by mixing a 60 weight % aqueous iodixanol solution (OptiPrep™ brand density gradient reagent, made by AXIS-SHIELD) with ET-Kyoto solution.

ET-Kyoto+ulinastatin+iodixanol solution (hereinafter also referred to as MI-Kyoto solution) was prepared by mixing 60 weight % aqueous iodixanol solution (OptiPrep™ brand density gradient reagent, made by AXIS-SHIELD plc) with M-Kyoto solution. ET-Kyoto+Pefabloc+iodixanol solution (hereinafter also referred to as Kyoto+AEBSF+Idx solution) was prepared by mixing 4-[2-aminoethylbenzenesulfonyl]fluoride·HCl (Pefabloc™ brand protease inhibitor, made by Roche Diagnostics) and 60 weight % aqueous iodixanol solution (OptiPrep™ brand density gradient reagent, made by AXIS-SHIELD plc) with ET-Kyoto solution.

The ET-Kyoto solution had a specific gravity of about 1.04 and the iodixanol solution had a specific gravity of approximately 1.32. When these were mixed, a light specific gravity of about 1.07 to 1.08 and a heavy specific gravity of 1.09 to 1.12 were prepared by changing the ratio between the two solutions.

2. Procedure for Porcine Islets Isolation

Porcine islets were isolated using the following procedure.

Porcine pancreatic tissues were obtained at a slaughterhouse in Kyoto. After pancreas procurement, (1) the pancreases were immediately preserved in a container in which two layers had been formed by the two-layer method or (2) a catheter was inserted into each pancreas immediately after procurement and pancreatic duct protection solution was injected through the catheter into the main pancreatic duct of each pancreas and the pancreases were thereafter quickly preserved in a container in which two layers had been formed by the two-layer method, the two layers being PFC and preservation solution. The volume of pancreatic duct protection solution injected in (2) was 1 mL per 1 gram pancreas weight.

Here, the time from heart beat cessation to immersion of the pancreas in the preservation solution is defined as the warm ischemic time. The time from immersion of the pancreas in the preservation solution to the start of islet separation is defined as the cold ischemic time.

The pancreas preserved by the two-layer method was transported to the islet isolation facility at the University of Kyoto and was then decontaminated.

A cold collagenase solution (Liberase HI™ brand enzyme blend, made by Roche Molecular Biochemicals) was then injected into the main duct of the pancreas and the pancreas was distended while the solution was circulated.

The distended pancreas was cut into nine pieces and placed in a Ricordi chamber. The circulation path in this chamber was filled with solution and the system was closed. Then, while circulating the solution with a pump, the temperature of the solution was raised to about 37° C. to activate the collagenase and the pancreatic tissue was digested by repeatedly circulating the collagenase solution through the Ricordi chamber. The digestion process was stopped at the point at which just the pancreatic exocrine tissue had been dissociated from around the islets while the cells making up the islets remained intact in their aggregated state.

To stop digestion, the collagenase was deactivated by lowering the temperature of the solution by opening the circulation path and passing a human-albumin-containing solution at room temperature through the circulation path.

The pancreatic tissue was recovered after digestion had been halted, by passage of the room temperature solution through the circulation path.

The time from placement of the pancreas in the Ricordi chamber to the start of recovery of the digested pancreatic tissue was designated as phase 1.

The time from the start of recovery until recovery was complete was designated as phase 2.

The recovered pancreatic tissue was centrifugally washed with a centrifugal separator and was aggregated and concentrated.

A continuous density gradient was formed in a blood cell washing instrument (COBE 2991 cell processor, Gambro BCT) using a purification solution that contained a density gradient reagent.

The washed and concentrated pancreatic tissue was then added to the solution in which the density gradient had been formed.

Purification was carried out by isolating the islets from the pancreatic tissue by carrying out centrifugal separation using the continuous density gradient and centrifugation technique to separate the islets from the pancreatic exocrine tissue. After this, the solution in the blood cell washing instrument was collected into individual fractions and a microscopic examination administered to determine which fractions the islets were present in, and the islets were then recovered.

3. Evaluation Methods

The islet yield and purity were evaluated by dithizone staining. After dithizone staining a 100 μL sample was taken from the solution suspended in 200 mL and the islet yield was evaluated under a microscope by individual sizes. The purity was given by the proportion of the islets in the total mass inclusive of all elements, e.g., islets, exocrine tissue in addition to the islets, pancreatic duct, and so forth.

The islet size was obtained as an average of the islets enumerated by individual sizes.

The efficiency of purification was obtained by dividing the number of islets after purification by the number of islets before purification.

The morphological score (gross morphological evaluation) was qualitatively assessed by having two investigators score the following: shape (flat versus spherical), border (irregular versus well-rounded), integrity (fragmented versus solid/compact), staining quality (uniform versus non-uniform), and diameter (all<100 μL versus>10%>200 μL). Each parameter was scored from 0 to 2 with 0 being the lowest score and 2 being the highest score. The lowest total score for islet isolation was therefore 0 and the highest was 10. Spherical, well-rounded, solid or compact, uniformly stained, and large diameter islets were characterized and scored as preferred islets.

Islet viability was assessed by the simultaneous visualization of live and dead cells using acridine orange (10 μmol/L) and propidium iodide (15 μmol/L) (AO/PI). 50 islets were investigated and the viability in each one was visually determined and the mean thereof was calculated.

The stimulation index was calculated from the ratio between insulin secretion at a high glucose concentration to that at a low glucose concentration.

Islet function was assessed according to the method of Shapiro and Colleagues by monitoring the insulin secretion response of the purified islets to glucose challenge. In brief, 100 Islet Equivalents (IE) were incubated on CMRL solution at 37° C. in a 5% $CO_2$ atmosphere and then incubated for 2 hours at 37° C. in a 5% $CO_2$ atmosphere on RPMI1640 solution (GIBCO BRL) containing 2.8 mM ether or 20 mM ether and 20 mM glucose; the supernatant was recovered and the insulin value was measured with an ELISA kit (Morinaga Biochemical Industry Co., Ltd.) using an antigen-antibody reaction.

The values obtained in the examples and experimental examples were reported using a mean and standard error (mean±SE). Comparisons were made among the three groups using the mean of ANOVA and Fisher's PLSD post-hoc test. Values with a P value less that 0.05 were taken as significant.

Example 1

Investigation of Pancreatic Duct Protection

Comparative experiments were carried out using the procedure described above in order to carry out a comparative investigation of the presence/absence of pancreatic duct protection. The procedures were identical, except that after pancreas procurement, (1) preservation by the two-layer method was immediately carried out (no pancreatic duct protection) or (2) protection solution was injected into the main duct of the pancreas immediately after procurement followed by preservation by the two-layer method (implementation of pancreatic duct protection).

In these experiments, M-Kyoto solution was used as the pancreatic duct protection solution. M-Kyoto solution and liquid PFC were used in the two-layer method. Ficoll solution was used as the purification solution.

Figure 1:
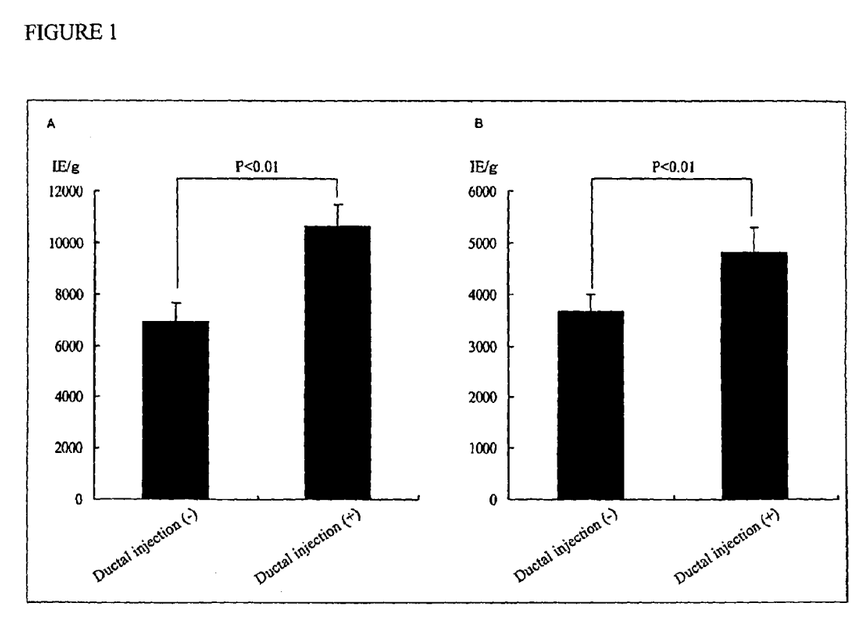
FIG. 1 shows the results of an experiment that compared islet yield with protection of the pancreatic duct against the islet yield without protection of the pancreatic duct. The islet yield before purification is shown in FIG. 1A. The islet yield after purification is shown in FIG. 1B. IE/g indicates the mean number of islets yielded per 1 gram pancreas. Ductal injection (−) shows the case in which protection solution was not injected into the pancreatic duct, while ductal injection (+) shows the case in which protection solution was injected into the pancreatic duct.

The islet yields obtained in these experiments before and after purification are shown in FIG. 1 (1A: Before purification, 1B: After purification) and the following table. IE/g denotes the mean number of islets per 1 gram pancreas.

TABLE 2

|  | Islet Yield (IE/g) | |
| --- | --- | --- |
|  | Before Purification | After Purification |
| No Pancreatic Duct Protection (−) | 6,889 ± 749 | 3,662 ± 320 |
| Implementation of Pancreatic Duct Protection (+) | 10,626 ± 2153 | 4,807 ± 1227 |

As shown in Table 2, both before purification and after purification, it was demonstrated that the islet yield with pancreatic duct protection (implementation of pancreatic duct protection) was significantly higher, than in the absence of pancreatic duct protection.

The other characteristics of the islets are shown in Table 3 below.

TABLE 3

|  | No Pancreatic Duct Protection (−) | Implementation of Pancreatic Duct Protection (+) |
| --- | --- | --- |
| Viability | 95.3 ± 1.5 | 96.2 ± 1.2 |
| Morphological score | 7.4 ± 0.7 | 7.8 ± 0.6 |
| Purity (%) | 86.3 ± 3.8 | 91.3 ± 4.3 |
| Stimulation Index | 1.7 ± 0.3 | 2.6 ± 1.4 |

As shown in Table 3, no significant difference was seen between the two groups with regard to the other islet characteristics.

Example 2

Comparative Investigations on Preservation by the Two-Layer Method

In order to perform comparative investigations of the use of different solutions in the two-layer method, comparative investigations were carried out using the same procedure, but using the different solutions shown in Table 4 for the two-layer method. The M-UW solution was obtained by adding 100,000 units (U) ulinastatin to 1 L UW solution.

The experiments were carried out using the following procedure.

Islets were isolated from inbred male Lewis rats weighing from 300 to 380 grams (Charles River Laboratories, Wilmington, Mass.). The rat studies were approved by the Review Committee of the Kyoto University Graduate School of Medicine. The common bile duct was cannulated using a 24-gauge catheter (Baxter, Deerfield, Ill.) and fixed and the end was then clamped. The pancreas, spleen, and duodenum were removed en bloc and preserved in the particular solution. The pancreas was preserved for 6 hours at 4° C. The islets were isolated using the modified method of Sawada (*Transplantation*. 2003; 75(12): 1965-1969). After preservation, each pancreas was distended using a 2 mg/mL collagenase solution (24 mg Serva collagenase, Serva, Heidelberg, Germany) in 12 mL Hanks' Balanced Salt Solution (HBSS). The spleen and duodenum were removed and the pancreas was incubated for 22 minutes at 37° C. in a 50 mL conical tube without shaking. The digested pancreas was washed three times with UW solution by centrifugal separation (150 g, 3 minutes, 8° C.). It was then purified with a discontinuous density gradient (1.030, 1.095, 1.105, 1.125 $g/cm^3$) formed using a solution of iodixanol (Optiprep™ brand density gradient reagent, Nycomed Pharma AS, Oslo, Norway) added to M-Kyoto solution. The resulting islet yield was assessed by dithizone staining.

Figure 2:
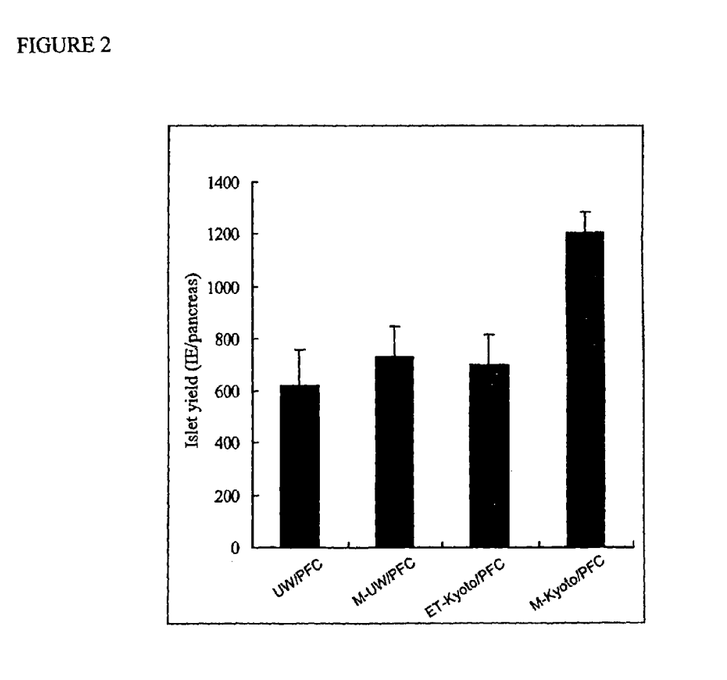
FIG. 2 shows the results of an experiment that compared the islet yield after purification for the use of different preservation solutions in the two-layer method. IE/pancreas shows the total yield of islets taken from a single pancreas. PFC refers to liquid perfluorocarbon (PFC); UW refers to UW solution; M-UW refers to UW+ulinastatin solution; ET-Kyoto refers to ET-Kyoto solution; and M-Kyoto refers to ET-Kyoto+ulinastatin solution.

The results of the post-purification islet yield are shown in FIG. 2 and Table 4. IE/pancreas denotes the total islet yield taken from each individual pancreas.

TABLE 4

| Solution Used in the Two-Layer Method | Post-Purification Islet Yield (IE/pancreas) |
| --- | --- |
| UW/PFC | 622 ± 133 |
| M-UW/PFC | 730 ± 114 |
| ET-Kyoto/PFC | 700 ± 116 |
| M-Kyoto/PFC | 1207 ± 76 |

As shown in Table 4 and FIG. 2, the post-purification islet yield was found to be significantly higher with the use of M-Kyoto solution for preservation in the two-layer method.

Example 3

Investigation of the Isolation Protocol 3-1. Protocol Outline

A comparative investigation was carried out using the following three isolation protocols in the porcine islet isolation procedure described above.

C1 Protocol

Injection of protection solution into the pancreatic duct was not carried out.

UW solution and liquid perfluorocarbon (PFC) were used in the two-layer method.

Ficoll solution was used as the purification solution.

C2 Protocol

Injection of protection solution into the pancreatic duct was carried out and pancreatic duct protection was implemented. M-Kyoto solution was used as the protection solution.

M-Kyoto solution and liquid perfluorocarbon (PFC) were used in the two-layer method.

Ficoll solution was used as the purification solution.

Kyoto Protocol

Injection of protection solution into the pancreatic duct was carried out and pancreatic duct protection was implemented. M-Kyoto solution was used for the protection solution.

M-Kyoto solution and liquid perfluorocarbon (PFC) were used in the two-layer method.

I-Kyoto solution was used as the purification solution. The features of each protocol are given in Table 5.

TABLE 5

| Protocol | Pancreatic Duct Protection | Solutions Used in the Two-Layer Method | Purification Solution |
| --- | --- | --- | --- |
| C1 protocol | No injection of protection solution | UW/PFC | Ficoll |
| C2 protocol | Injection of M-Kyoto solution | M-Kyoto solution/PFC | Ficoll |
| Kyoto protocol | Injection of M-Kyoto solution | M-Kyoto solution/PFC | I-Kyoto solution |

3.2. Comparison of Protocols 3.2(1). Characteristics of the Isolation Processes

The characteristics of the isolation process are shown in Table 6 for each protocol.

TABLE 6

|  | C1 Protocol | C2 Protocol | Kyoto Protocol |
| --- | --- | --- | --- |
| Pancreas Size (g) | 104 ± 13 | 105 ± 8 | 104 ± 8 |
| Operation Time (min) | 9 ± 1 | 13 ± 1 | 13 ± 1 |
| Warm Ischemic Time (min) | 19 ± 1* | 24 ± 2 | 25 ± 1 |
| Cold Ischemic Time (min) | 148 ± 9** | 120 ± 0 | 120 ± 0 |
| Phase 1 Period (min) | 13 ± 1*** | 8 ± 1 | 8 ± 1 |
| Phase 2 Period (min) | 27 ± 1 | 38 ± 4 | 34 ± 3 |

The * in the table indicates that the warm ischemic time for the C1 protocol was significantly shorter than the C2 protocol ($P < 0.01$) and the Kyoto protocol ($P < 0.01$).
The ** in the table indicates that the cold ischemic time for the C1 protocol was significantly longer than for the C2 protocol ($P < 0.01$) and the Kyoto protocol ($P < 0.01$).
The *** in the table indicates that phase 1 for the C1 protocol was significantly longer than for the C2 protocol ($P < 0.02$) and the Kyoto protocol ($P < 0.01$).

There was no substantial difference in pancreas size or operation time among the three groups.

The C1 protocol, because it lacked the step of injection into the pancreatic duct, had a significantly shorter warm ischemic time than the other protocols. However, the C1 protocol had a significantly longer cold ischemic time than the other protocols because it required catheter insertion.

Phase 1 was particularly long with the C1 protocol. However, phase 2 was about the same among the three groups.

3-2(2). Islet Yields

The islet yields before and after purification in the individual isolation protocols are shown in Table 7 below and in FIGS. 3A and 3B. IE/g denotes the mean number of islets yielded per 1 gram pancreas.

TABLE 7

|  | Islet Yield (IE/g) | |
| --- | --- | --- |
|  | Before Purification | After Purification |
| C1 Protocol | 4,809 ± 454 IE/g | 2,486 ± 394 IE/g |
| C2 Protocol | 8,846 ± 904 IE/g | 3,527 ± 795 IE/g |
| Kyoto Protocol | 10,247 ± 637 IE/g | 7,253 ± 915 IE/g |

Figure 3:
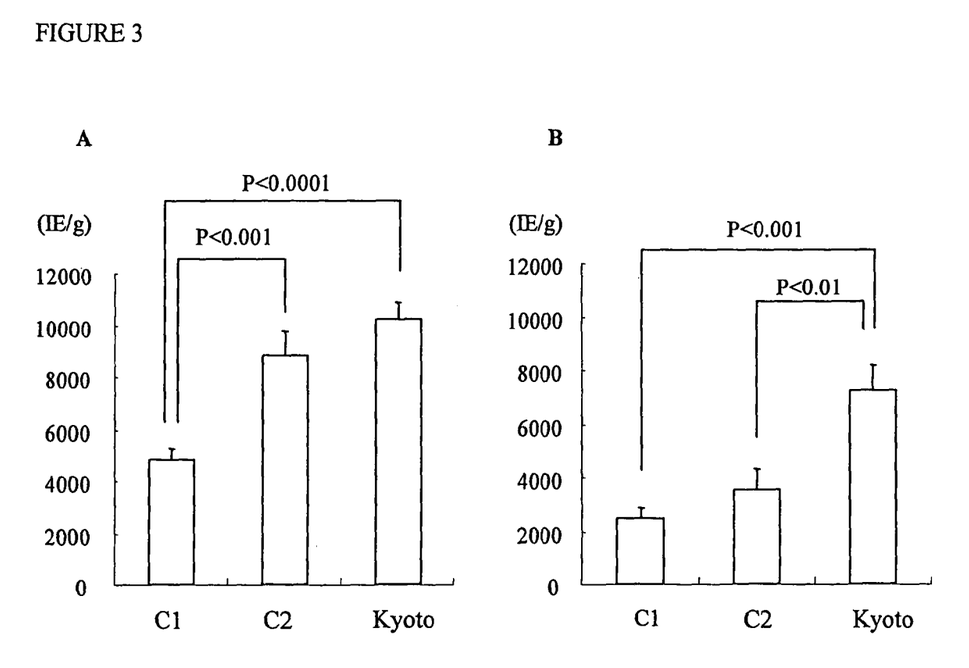
FIG. 3 shows the results for islet yield in porcine islet isolation with a comparison of individual protocols. The pre-purification results are shown in FIG. 3A. The post-purification results are shown in FIG. 3B. IE/g indicates the mean number of islets yielded per 1 gram pancreas.

As shown in Table 7 and FIG. 3, the values for the islet yield before purification were significantly higher in the C2 protocol and the Kyoto protocol than in the C1 protocol (FIG. 3A).

In addition, the value of the islet yield after purification was significantly higher in the Kyoto protocol than in the C1 protocol and C2 protocol (FIG. 3B).

3-2(3). Islet Characteristics

The characteristics of the isolated islets are shown in Table 8 below.

TABLE 8

|  | C1 Protocol | C2 Protocol | Kyoto Protocol |
|---|---|---|---|
| Viability (%) | 93 ± 4 | 96 ± 1 | 96 ± 1 |
| Morphological score | 6.9 ± 0.6 | 7.8 ± 0.6 | 8.8 ± 0.6* |
| Purity (%) | 93 ± 1 | 86 ± 5 | 78 ± 9 |
| Efficiency of purification (%) | 51 ± 5 | 38 ± 6 | 64 ± 6** |
| Pre-Purification Islet Size (μm) | 146 ± 16 | 152 ± 16 | 176 ± 12 |
| Post-Purification Islet Size (μm) | 113 ± 33 | 83 ± 11 | 211 ± 55*** |
| Stimulation Index | 1.4 ± 0.9 | 1.4 ± 0.4 | 1.6 ± 0.3 |

The * in the table indicates that the Kyoto protocol gave a substantially higher morphological score than the C1 protocol ($P < 0.03$).
The ** in the table indicates that the Kyoto protocol gave a substantially higher efficiency of purification than the C1 protocol ($P < 0.05$) and the C2 protocol ($P < 0.01$).
The *** in the table indicates that the Kyoto protocol gave a substantially larger post-purification islet size than the C2 protocol ($P < 0.04$).

As shown in Table 8, there was no significant difference in stimulation index, viability, purity, or pre-purification islet size among the three groups.

However, it was found that the results with the Kyoto protocol for the morphological score, efficiency of purification, and post-purification islet size were particularly good.

3-2(4). Purification Speed

The purification speeds in the individual isolation protocols were investigated. As a result, it was found that the purification solution could be delivered into the COBE 2991 cell processor at a rate of 60 ml/min in the Kyoto protocol.

Against this, the purification solution delivery rate in the C1 and C2 protocols, which used Ficoll solution as the purification solution, was 10 to 20 ml/min.

These results showed that the rate of islet purification could be speed up by 3- to 6-fold using iodixanol as the density gradient reagent. The primary factor for this result was thought to be the low viscosity of the purification solution when iodixanol was used.

Example 4

Investigation of Protease Inhibitor

The following experiment was carried out in order to examine the type of protease inhibitor.

Islet yield was assessed using the same procedure as described above for the Kyoto protocol, with the exception that the solutions described in Table 9 were used for the protection solution injected into the main pancreatic duct and the preservation solution in the two-layer method.

TABLE 9

| Protection Solution and Preservation Solution | Islet Yield (IE/g) |
|---|---|
| ET-Kyoto Solution | 2103 |
| ET-Kyoto + AEBSF Solution | 3448 |

TABLE 9-continued

| Protection Solution and Preservation Solution | Islet Yield (IE/g) |
|---|---|
| M-Kyoto Solution (ET-Kyoto + Ulinastatin Solution) | 7253 |
| ET-Kyoto + Gabexate Mesilate Solution | 7140 |

These results demonstrate that islet yield was increased when a protease inhibitor was added to the protection solution injected into the pancreatic duct.

It was found in particular that islet yield was substantially raised when the protease inhibitor was ulinastatin or gabexate mesilate.

In addition, the use of ET-Kyoto+gabexate mesilate solution as the protection solution injected into the main pancreatic duct and as the preservation solution in the two-layer method yielded a purity of 89% and a viability of 90% for the isolated islets.

Example 5

Investigation of Purification

Further investigations were carried out using different purification solutions as follows.

The efficiency of purification was assessed by the method described above using the Kyoto protocol described in the above porcine islet isolation procedure, with the exception that the purification solutions shown in Table 10 were used.

TABLE 10

| Purification Solution | Efficiency of purification (%) |
|---|---|
| I-Kyoto Solution | 64 |
| I-Kyoto + AEBSF Solution | 70 |
| MI-Kyoto Solution (I-Kyoto + ulinastatin solution) | 80 |

As is shown in Table 10, the efficiency of purification was found to be increased when a protease-inhibitor-containing solution was used as the purification solution.

In particular, the use of MI-Kyoto solution, that is, the use of ulinastatin as the protease inhibitor, was found to provide a substantial increase in efficiency of purification.

Further, just as for the use of 1-Kyoto solution, the use of MI-Kyoto solution also enabled the purification solution to be delivered into the COBE 2991 cell processor at a rate of 60 ml/min.

Example 6

Human Islet Isolation 6-1. Procedure for Human Islet Isolation

Human islet isolation was carried out using the same procedure as for porcine islet isolation, except for the points noted below.

With informed consent in place, thirteen human pancreases were acquired from non-heart-beating donors through the Central Japan Region and the Western Japan Region of the Japan Organ Transplant Network.

A catheter was inserted in order to rapidly cool the pancreases via the blood vessels of the donor's inguinal region and cold lactated Ringer's solution was injected through this catheter and circulated from after heart beat cessation until removal of the pancreas.

The pancreases were then removed and a catheter was immediately inserted and M-Kyoto solution was injected into the main pancreatic duct at the rate of 1 ml per 1 gram pancreas weight. This was quickly followed by immersion of the pancreases in the preservation solution of a two-layer method preservation container. The pancreases were then transported to the GMP-grade Center for Cell and Molecular Therapy at Kyoto University. The two-layer method used M-Kyoto solution and liquid perfluorocarbon (PFC).

The assessment procedures were the same as in the previously described porcine islet isolation procedure. Statistical evaluation was also the same as for porcine islet isolation.

6-2. Isolation Protocol

Isolation of human islets was carried out by the C2 protocol in 2 of the thirteen cases and was carried out by the Kyoto protocol in 11 of the thirteen cases.

6-3. Characteristics of Human Donors and Pancreases

The mean donor age was 44±4 years. The period of ICU stay was 11±3 days. The BMI was 21±1 kg/m². The pancreas size was 87±6 g. Abnormalities were observed in the average blood chemistry values of all the donors.

The warm ischemic time was 7±3 minutes. The cold ischemic time was 256±18 minutes. The warm ischemic time for all the pancreases was minimized by the immediate circulation with cold lactated Ringer's solution. In addition, the cold ischemic time was shorter than 6 hours in all cases.

There were no significant differences between the two protocols with regard to donor conditions, warm ischemic time, and cold ischemic time.

6-4. Assessment of Isolation Protocols

The results of the assessment of human islet isolation are shown in Table 11 for the two protocols (C2 protocol, Kyoto protocol). The islet yield (IE) indicates the total islet yield.

TABLE 11

|  | C2 Protocol (N = 2) | Kyoto Protocol (N = 11) |
|---|---|---|
| Pre-Purification Islet Yield (IE) | 733,620 ± 249,440 | 526,657 ± 67,695 |
| Post-Purification Islet Yield (IE) | 339,480 ± 14,905 | 410,376 ± 42,412 |
| Efficiency of purification (%) | 51 ± 15 | 81 ± 5 |
| Purity (%) | 50 ± 10 | 51 ± 6 |
| Viability (%) | 94 ± 6 | 97 ± 1 |
| Morphological score | 9.0 ± 1.0 | 9.8 ± 0.1 |
| Tissue Volume (mL) | 8.0 ± 1.0 | 6.4 ± 0.8 |
| Negative Gram Stain | 2/2 | 11/11 |
| Endotoxin (EU) | 14.4 ± 11.0 | 8.7 ± 3.6 |
| Transplant Criteria Qualification | 2/2 | 11/11 |
| Transplanted | 1/2 | 10/11 |

There were no significant differences between the two protocols in the pre-purification islet yield or post-purification islet yield. The same results are also obtained in the purity, viability, and morphological score between the two protocols.

The efficiency of purification was 1.6-times higher in the Kyoto protocol than in the C2 protocol. The endotoxin level was lower for the Kyoto protocol than for the C2 protocol.

With regard to the purification speed, the purification solution could be delivered into the COBE 2991 cell processor at the rate of 60 ml/min in the Kyoto protocol. This rate was 10 to 20 ml/min for the C2 protocol.

Based on these results, it was confirmed that the use of 1-Kyoto solution as the purification solution also provides a 3- to 6-times faster islet purification speed in human islet isolation.

The following tests were also carried out with the purification solution.

The efficiency of purification and islet yield were assessed using the same procedures as the Kyoto protocol in the above-described human islet isolation, except that the purification solutions shown in Table 12 were used.

TABLE 12

| Purification Solution | Efficiency of purification (%) | Total Islet Yield (IE) |
|---|---|---|
| I-Kyoto Solution | 78 | 479409 |
| MI-Kyoto Solution | 84.2 | 544535 |

As shown in Table 12, it was found that the efficiency of purification was also raised in human islet isolation when a protease-inhibitor-containing solution was used as the purification solution. It was additionally found that the islet yield was also raised.

6-5. Transplant Qualifying Criteria

The following transplant qualifying criteria were established based on the Edmonton protocol.

Islet Yield≧5,000 IE/kg (patient body weight)
Purity≧30%
Tissue volume≦10 mL
Viability≧70%
Endotoxin≦5 IE/kg (patient body weight)
Negative Gram stain With regard to these criteria, all thirteen cases satisfied the transplant qualifying criteria, with the exception of islet yield.

6-6. Islet Transplantation into Type-I Diabetic Patients

Of the thirteen cases described above, eleven cases, that is, one case of those islets isolated according to the C2 protocol and ten cases of those islets isolated according to the Kyoto protocol were transplanted into six type-I diabetic patients. The islets isolated in the remaining two cases were cryopreserved.

Four of the six patients received multiple-donor islet transplants. Two patients received single-donor islet transplants.

The assessments made after islet transplantation were carried out using the following methods.

The serum blood glucose, insulin requirement, and hemoglobin Alc (HbAlc) were assessed daily before and after transplantation. The glucagon stimulation test was carried out before transplantation, on the $30^{th}$ and 60th day after the first transplantation, and on the $30^{th}$ day and $60^{th}$ day after the second transplantation. In the glucagon stimulation test, blood was taken for C-peptide measurement immediately before the injection of 1 mg glucagon and 6 minutes after the injection.

6-7. Assessment After Islet Transplantation

After islet transplantation, none of the six patients suffered from hypoglycemic unawareness and an improved blood glucose control could be observed in all six. In addition, the start of insulin secretion was confirmed in all of the transplant cases based on C-peptide measurement.

While the mean insulin amount was 39.2±3.2 units at the time of transplantation, it fell to 11.0±4.4 units (P<0.0005). Two patients became insulin free; in two other patients the amount of insulin declined to below 10 units; and in the two other patients the amount of insulin also declined.

Figure 4:
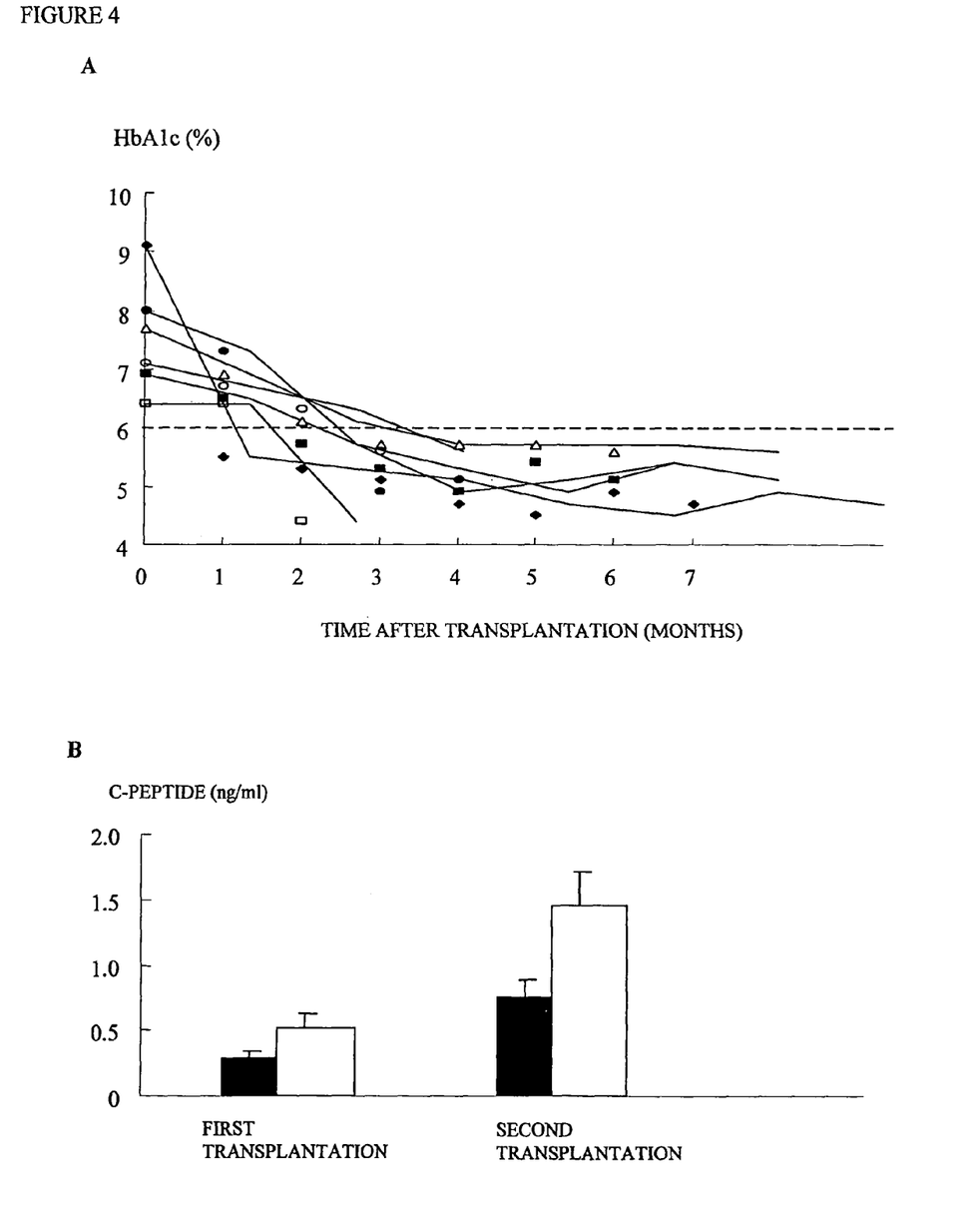
FIG. 4A shows the change in the HbAlc value for 6 patients pre- and post-transplantation from non-heart-beating donors. A different symbol is used to show the data for each patient. The y-axis in FIG. 4A shows the percentage HbAlc with reference to the total hemoglobin. The dashed line shows the upper limit for normal values.
FIG. 4B shows the C-peptide value (mean value) in the glucagon stimulation test. The filled square (■) shows the basal value and the open square (□) shows the value after stimulation.

The HbAlC level gradually declined in all six patients, and in all six patients the HbAlc level reached normal at about 3 months after islet transplantation, regardless of whether the transplantation was from a single donor or multiple donors (FIG. 4A).

The mean HbA1c level of the six patients underwent substantial improvement, improving from 7.5±0.4% at the time of transplantation to 5.1±0.2% (P<0.0003).

Prior to transplantation, all the patients had undetectable C-peptide values (<0.1 ng/ml), while post-transplant the C-peptide values could be detected. With regard to the C-peptide values after the first transplantation, the basal value was 0.29±0.06 ng/ml and the post-stimulation value was 0.52±0.11 ng/ml (N=6) (FIG. 4B). Both the basal C-peptide value and the post-stimulation C-peptide value were substantially improved after the second islet transplantation from the values for the first transplantation. After the second transplantation, the basal C-peptide value was 0.75±0.12 ng/ml (P<0.01) and the post-stimulation value was 1.45±0.26 ng/ml (P<0.005) (N=3) (FIG. 4B).

6-8. Clinical Islet Transplantation

Islet transplantation was carried out in a clinical setting in accordance with the Kyoto protocol described above. A second transplantation was carried out in the same manner on the same patient after about 2 months.

The islet yield for the first transplantation was 354,384 IE and for the second transplantation was 474,234 IE.

The recipient was a 36-year-old female with a 22-year history of type I diabetes; there had been frequent episodes of severe hypoglycemia and there was a history of diabetic retinopathy.

Kidney function was normal and creatinine level was 0.7 mg/dl. Immunosuppressives were administered on day 0 and day 4 post-transplantation in accordance with the Edmonton protocol, with the exception that 20 mg basiliximab was used instead of daclizumab.

To provide a pre-transplantation blood glucose level control, blood glucose was measured before breakfast and before dinner at approximately 2 month intervals for approximately the preceding 2 years.

Blood glucose prior to islet transplantation was very unstable and ranged broadly from 20 mg/dl to 400 mg/dl.

Figure 5:
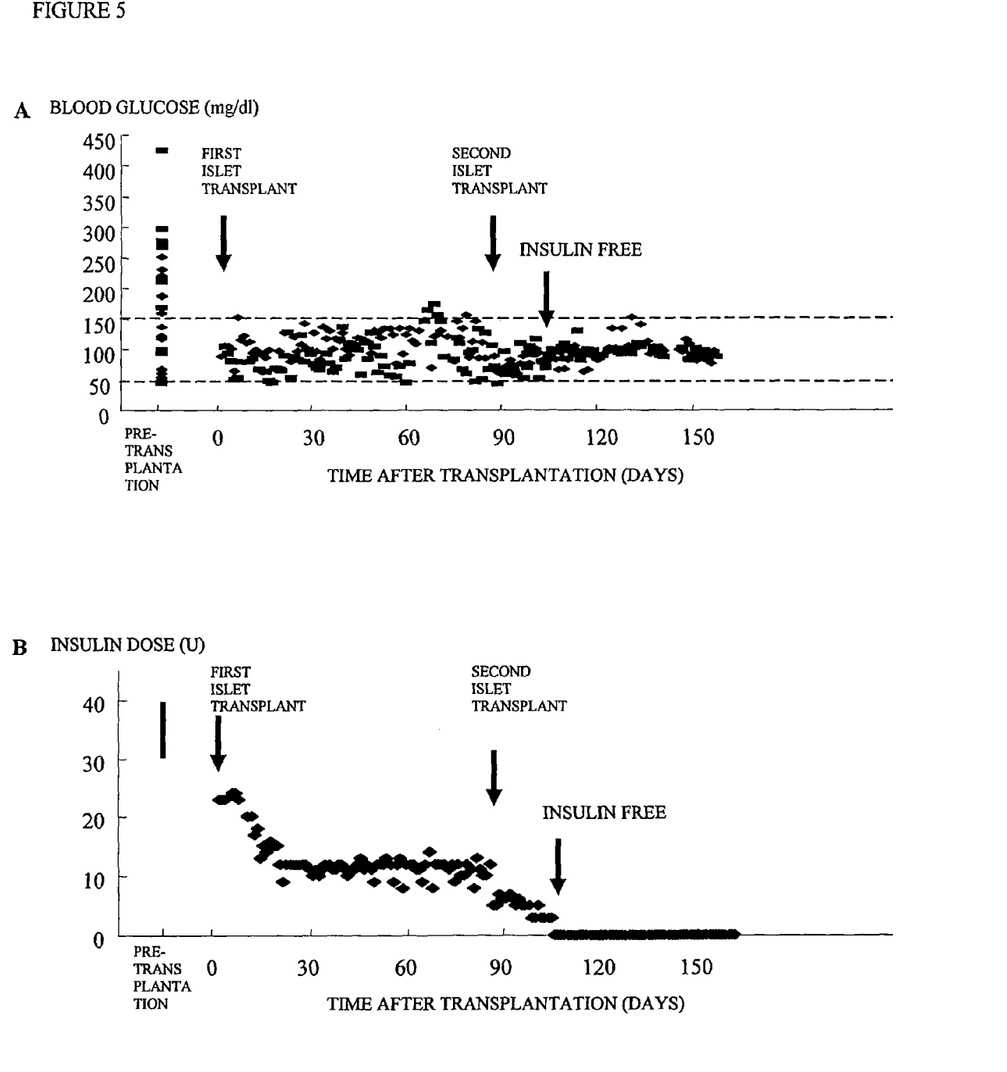
FIG. 5A shows the results of measurement before and after islet transplantation of blood glucose value before breakfast and before dinner. The two dashed lines in FIG. 5A indicate the normal range. The filled diamonds (♦) show the values before breakfast, while the filled squares (■) show the values before dinner.
FIG. 5B shows the daily amount of insulin for a patient before and after islet transplantation.

After the first transplantation, however, blood glucose was maintained in a narrow range and settled into a narrow range from 50 mg/dL to 150 mg/dL (FIG. 5A).

The pre-transplantation insulin requirement was from 30 to 40 unit/day; however, the insulin intake gradually declined to 10 unit/day by 1 month after the first transplantation. Moreover, the patient was able to completely stop and achieve insulin free on day 20 after the second transplantation (FIG. 5B).

The transaminase value temporarily increased after the first transplantation, but did not reach or exceed 100 mg/dl and returned to normal values within 3 weeks. The creatinine value remained at or below 1.0 mg/dl, and blood urea nitrogen (BUN) stayed at normal values during the entire period of observation.

As is clear from the results given above, the present invention has been shown to raise efficiency of purification and to raise the yield of islets that satisfy the transplant qualifying criteria. In addition, the present invention has been shown to raise the purification speed and to enable islet isolation with good efficiency in a short period of time.

Moreover, the present invention has been shown to have the ability to acquire good amounts of good-quality islets from non-heart-beating donors. The present invention has also been shown to be highly successful with regard to islet transplantation from human non-heart-beating donors.

The invention claimed is:

1. A pancreatic islet isolation method comprising the sequential steps of:
    (1) injecting a protection solution containing a protease inhibitor and approximately 4 to 50 mmol/L of potassium into the pancreatic duct of a procured pancreas, wherein said protease inhibitor is at least one selected from the group consisting of ulinastatin, gabexate mesilate and nafamostat mesilate;
    (2) preserving said pancreas into which the protection solution has been injected by a two-layer method that comprises introducing (i) a liquid perfluorocarbon and (ii) a preservation solution containing a protease inhibitor, approximately 4 to 50 mmol/L of potassium, and 80 to 160 mmol/L of trehalose into a container and forming two layers, feeding oxygen into the container, and preserving said pancreas in said container;
    (3) injecting a collagenase solution into said pancreas into which the protection solution has been injected and digesting the pancreas; and
    (4) purifying the digested pancreatic tissue using a purification solution containing a density gradient reagent wherein said density gradient reagent is Ficoll solution or iodixanol.

2. The isolation method according to claim 1, wherein the protection solution is injected into the pancreatic duct in an amount of approximately 0.1 to 10 ml per 1 gram organ weight in step (1).

3. The isolation method according to claim 1, wherein the purification solution in step (4) further contains trehalose.

4. The isolation method according to claim 1, wherein the density gradient reagent in step (4) is iodixanol.

5. The isolation method according to claim 1, wherein the purification solution in step (4) further contains a protease inhibitor.

6. The method according to claim 1, wherein in step (1) said protease inhibitor is ulinastatin.

7. The method according to claim 1, wherein in step (1) said protease inhibitor is gabexate mesilate.

8. The method according to claim 1, wherein in step (1) said protease inhibitor is nafamostat mesilate.

* * * * *

UNITED STATES PATENT AND TRADEMARK OFFICE
CERTIFICATE OF CORRECTION

PATENT NO. : 8,288,085 B2
APPLICATION NO. : 11/793679
DATED : October 16, 2012
INVENTOR(S) : Shinichi Matsumoto, Hiromi Wada and Hirofumi Noguchi It is certified that error appears in the above-identified patent and that said Letters Patent is hereby corrected as shown below:

On the title page item [73] should read: Otsuka Pharmaceutical Factory, Inc.
Tokushima (JP)

Signed and Sealed this
Twenty-third Day of July, 2013

Teresa Stanek Rea
*Acting Director of the United States Patent and Trademark Office*